(12) United States Patent
Martino (10) Patent No.: US 10,973,453 B2
(45) Date of Patent: Apr. 13, 2021

(54) HAND HELD SMELL TEST (71) Applicant: SENSONICS, INC., Haddon Heights, NJ (US)

(72) Inventor: Dominick Daniel Martino, Levittown, PA (US)

(73) Assignee: Sensonics, Inc., Haddon Heights, NJ (US)

( * ) Notice: Subject to any disclaimer, the term of this patent is extended or adjusted under 35 U.S.C. 154(b) by 968 days.

(21) Appl. No.: 14/783,510

(22) PCT Filed: Apr. 1, 2014

(86) PCT No.: PCT/US2014/032449
§ 371 (c)(1),
(2) Date: Oct. 9, 2015

(87) PCT Pub. No.: WO2014/168783
PCT Pub. Date: Oct. 16, 2014

(65) Prior Publication Data
US 2016/0095544 A1    Apr. 7, 2016

Related U.S. Application Data (60) Provisional application No. 61/810,898, filed on Apr. 11, 2013.

(51) Int. Cl.
| | | |
|---|---|---|
| *A61B 5/00* | (2006.01) |
| *A61L 9/12* | (2006.01) |
| *G01N 33/00* | (2006.01) |
| *A61M 15/08* | (2006.01) |
| *A61M 15/06* | (2006.01) |

(52) U.S. Cl.
CPC ............ *A61B 5/4011* (2013.01); *A61L 9/127* (2013.01); *G01N 33/0001* (2013.01); *A61B 2560/0418* (2013.01); *A61L 2209/134* (2013.01); *A61M 15/06* (2013.01); *A61M 15/08* (2013.01)

(58) Field of Classification Search
None
See application file for complete search history.

(56) References Cited

U.S. PATENT DOCUMENTS

2,809,634 A    10/1957  Murai
4,084,726 A     4/1978  Nicol
(Continued)

*Primary Examiner* — Kaylee R Wilson
*Assistant Examiner* — Jay B Shah
(74) *Attorney, Agent, or Firm* — Norman E. Lehrer (57) ABSTRACT

A hand held olfactory tester includes an elongated housing (12) with an opening at its forward end (30) thereof. An odorant chamber (22) located within the housing moveable axially between a forward (FIG. 4) and a backward position (FIG. 5). A wick (34) extends from the odorant chamber forwardly into a nozzle (32) carried at the forward end of the chamber. A thumb collar (24) located around the outside of the housing allows to move the odor chamber and nozzle forwardly. The forward end of the wick exposed to outside through the opening when moved forward so that vapors from the odorant can be smelled by a patient. O-rings (40, 42) seal the nozzle from the outside when in backward position to prevent vapors from escaping. An elongated spring (28) biases the odorant chamber and nozzle backwardly into its rear sealed position when the thumb collar is released.

8 Claims, 6 Drawing Sheets

(56) References Cited

U.S. PATENT DOCUMENTS

| | | | |
|---|---|---|---|
| 5,048,720 A | 9/1991 | Hoke | |
| 5,565,148 A | 10/1996 | Pendergrass, Jr. | |
| 6,132,830 A | 10/2000 | O'Halloran | |
| 6,174,251 B1 | 1/2001 | Lemote | |
| 6,231,256 B1 | 5/2001 | Kingsford et al. | |
| 8,250,903 B2 | 8/2012 | McDevitt et al. | |
| 2002/0066967 A1* | 6/2002 | Bartsch | A01M 1/2033 261/26 |
| 2004/0068916 A1* | 4/2004 | Harris | A01K 97/02 43/44.99 |
| 2004/0112378 A1* | 6/2004 | Djupesland | A61B 5/085 128/203.12 |
| 2008/0313789 A1 | 12/2008 | Manne | |
| 2009/0152306 A1* | 6/2009 | Pardes | B65D 47/205 222/494 |
| 2012/0247182 A1 | 10/2012 | Nelson | |

\* cited by examiner

HAND HELD SMELL TEST

TECHNICAL FIELD

The present invention is directed toward devices for use in administering olfactory or smell tests. The devices are hand held and operated and can be used in threshold tests, discrimination tests and identification tests.

BACKGROUND ART

The ability to smell various odors and to distinguish odors from each other is obviously important in our every day lives. The sense of smell, which largely influences the flavor of foods, is associated with emotion, with nutrition, with quality of life, and with safety from spoiled foods, leaking natural gas, fire, and other hazardous situations. Loss of smell or the reduced ability to smell, therefore, can significantly impact everyday life. People who lose the sense of smell have major elements of their lives compromised and often become psychologically depressed.

Quantitative tests of the sense of smell can also be useful as diagnostic tools. The measurement of olfactory thresholds, for example, is beneficial in the early detection and management of a number of diseases and disorders. Among these are damage to the olfactory system, such as the olfactory nerves or olfactory bulb, by head trauma, neurodegenerative diseases such as Alzheimer's disease and Parkinson's disease, acute viral and/or bacterial infections, exposure to toxic fumes and chemicals, side-effects from radiation therapy to the head, and others. A medical diagnostic instrument that can measure olfactory thresholds and other indices of olfactory function in an accurate manner, quickly and at a relatively low cost, would therefore be beneficial. Such an instrument could be used not only as a one time evaluation of a patient, but it could be used to trace a patient's progress over time to monitor for onset of a particular occurrence.

The measurement of olfactory function has been accomplished by various means. Olfactometers have been developed in the past for administering smell tests. One such device was commercially available from Osmic Enterprises, Inc. of Cincinnati, Ohio, and allegedly was useful for assessing odor threshold, identification, discrimination, and memory. Smaller, less complicated, olfactometers have also been proposed and are described in various patent documents. For example, the following U.S. Patents have issued for alleged improvements to olfactometers: 4,265,248 to Chuiton et al.; 5,565,148 to Pento Fadergrass, Jr.; 6,390,453 and 6,672,129 to Frederickson et al. and 7,152,758 to Fazzio et al.

The olfactometer or odor generator described in Applicant's U.S. patent application Ser. No. 12/799,034, solves many of the problems associated with other prior art olfactometers and is believed to be the most effective and device available. However, it is relatively expensive and is primarily used by a research facility or the like.

Much simpler tests and devices that can be administered in a doctor's office have also been proposed. One method is by using scratch-and-sniff pads where the test operator scratches the surface to expose the odor, puts it up to the patient's nose, and asks for a response. Another test method is using squeeze-bottle or sniff bottle smell test kits. In the case of threshold testing, a series of bottles with increasing concentration of vapors is used.

Also available is a test sold under the name Sniffin' Sticks which is comprised of a number of tubular containers having an odorant therein and a wicking member that extends from the end of the tube but which is covered by an end cap. Two hands are needed to administer a test as the end cap must be removed with one hand whiled holding the tube with the other. Furthermore, if the end cap is not replaced, the odorant within the tube will dry out.

There is, therefore, a need for an improved hand held olfactory test that is effective, relatively inexpensive and easy to administer.

DISCLOSURE OF THE INVENTION

The present invention is designed to overcome the deficiencies of the prior art discussed above. According to the invention, a hand held olfactory tester includes an elongated housing with an opening at its forward end thereof. Located within the housing is an odorant chamber moveable axially between a forward position and a backward position. A wick extends from the odorant chamber forwardly into a nozzle carried at the forward end of the chamber. A thumb collar located around the outside of the housing allows a person to move the odor chamber and nozzle forwardly. The forward end of the wick is exposed to the outside through the housing opening when moved forward so that vapors from the odorant can be smelled by a patient. O-rings seal the nozzle from the outside when it is in its backward position to prevent vapors from escaping. An elongated spring biases the odorant chamber and nozzle backwardly into its rear sealed position when the thumb collar is released.

BRIEF DESCRIPTION OF THE DRAWINGS

For the purpose of illustrating the invention, there is shown in the accompanying drawings forms which are presently preferred; it being understood that the invention is not intended to be limited to the precise arrangements and instrumentalities shown.

BEST MODE FOR CARRYING OUT THE INVENTION

Referring now to the drawings in detail wherein like reference numerals have been used throughout the various figures to designate like elements, there is shown in FIGS. 1-6 a hand held olfactory tester constructed in accordance with the principles of the present invention and designated generally as 10. While only one such device is shown in the drawings, it will be understood by those skilled in the art that numerous similar devices will be provided in order to perform a smell test. The several devices may have either different odorants therein or different concentrations of the same or different odorants.

The tester 10 is comprised essentially of a cylindrically shaped housing 12 having an outer cylindrical surface 14 and an inner cavity 16. The overall shape and appearance of the device 10 resembles a writing pen and is constructed and arranged so as to be capable of being held and manipulated with only one hand of the doctor or other person administering a smell test.

Located in the forward end 18 of the inner cavity 16 is an odorant cylinder 20 having a chamber 22 therein. A liquid odorant (not shown) is contained within the chamber 22. The use of a liquid is, of course, by way of example only. Solid or gaseous odorants are also possible. It is also possible to fill the chamber 22 with absorbent material to hold the liquid.

In any event, the cylinder 20 is axially movable within the inner cavity 16. It can be moved forwardly, i.e. to the left in FIGS. 1-4, by pushing on the collar 24. This is preferably done by a person holding the outer cylindrical surface 14 at the rear end 26 of the housing 12 while pushing the collar 24 with his or her thumb. In lieu of pushing a collar, it may also be possible to employ a slide button or the like. It is also not beyond the scope of the invention to include a thread or spiral arrangement whereby twisting the forward end 18 causes the odorant cylinder 20 to move forward. Even further, a small electric motor or an electric solenoid could be employed to move the odorant cylinder 20 when a switch of button is depressed.

Pushing the collar 24 forward will move the odorant cylinder 20 forward against the force of the spring 28. Preferably, an audio cue or alert will indicate when the collar has been moved forward into its proper position. This can be accomplished using any known device such as a snap washer or the like. When the thumb is released from the collar 24, the force of the spring 28 will cause the odor cartridge 20 to retreat backwardly to its original position.

The forwardmost end 30 of the housing 12 preferably tapers down to a smaller cross section. Similarly, the forward end of the odor cylinder 20 tapers down to a shape which is substantially complementary to the forward end 30 of the housing and functions as a nozzle 32. As should be obvious to those skilled in the art, the nozzle 32 can be a separate device that is secured to the cylinder 20 in a known manner.

Extending between the interior 22 of the odor chamber and the interior of the nozzle 32 is a wick 34. The wick 34 can be made from essentially any known wicking material such as various compressed fibers or porous plastics or the like. The wick 34 delivers a liquid odorant from the chamber 22 to the interior of the nozzle 32 and terminates in what is commonly referred to as a nib shown most clearly in FIG. 3 at 36.

Figure 1:
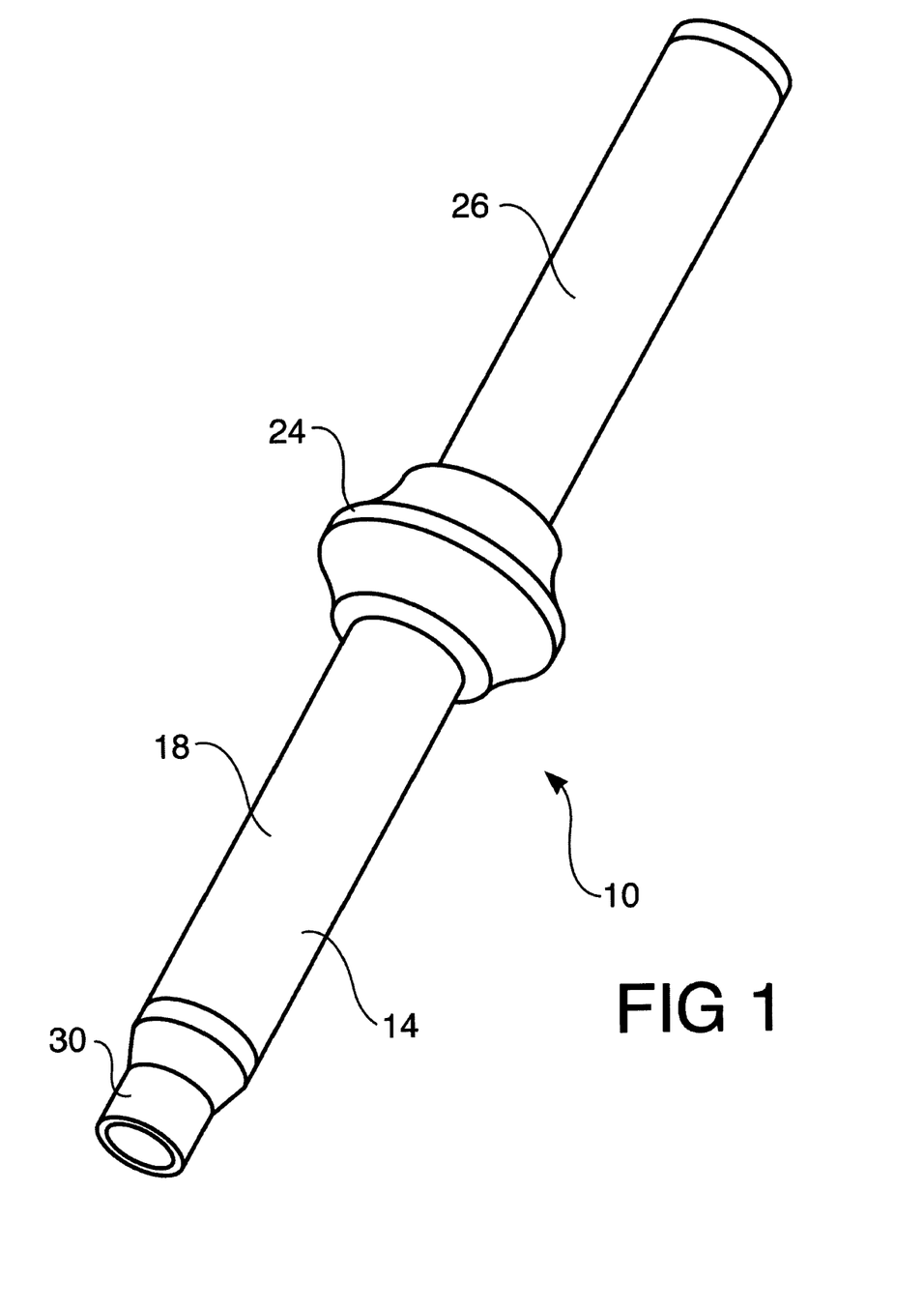
FIG. 1 is a perspective view of a hand held olfactory tester of the present invention and shown in a closed position.
Figure 2:
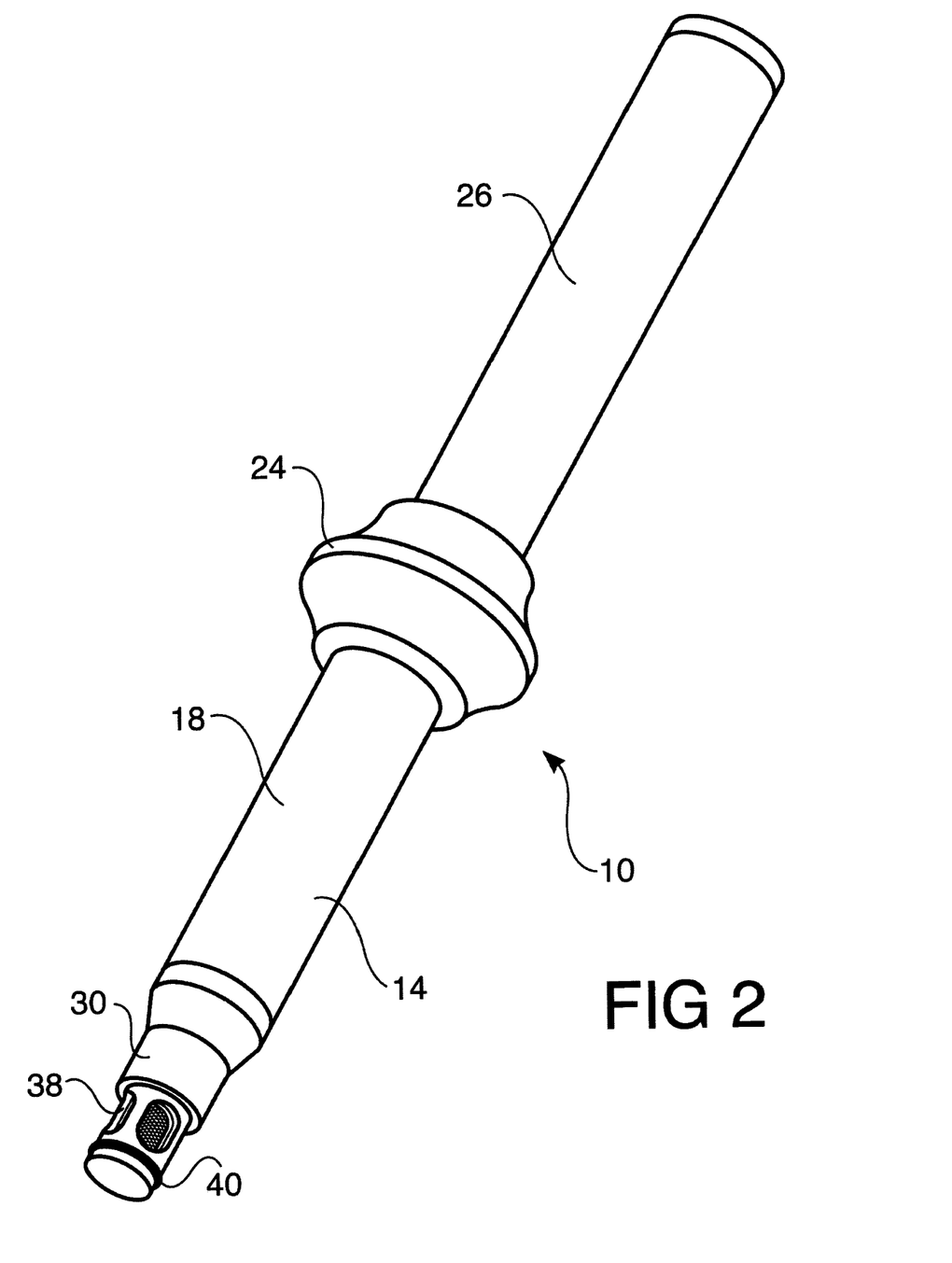
FIG. 2 is a perspective view similar to FIG. 1 but showing the tester in an open or testing position.
Figure 3:
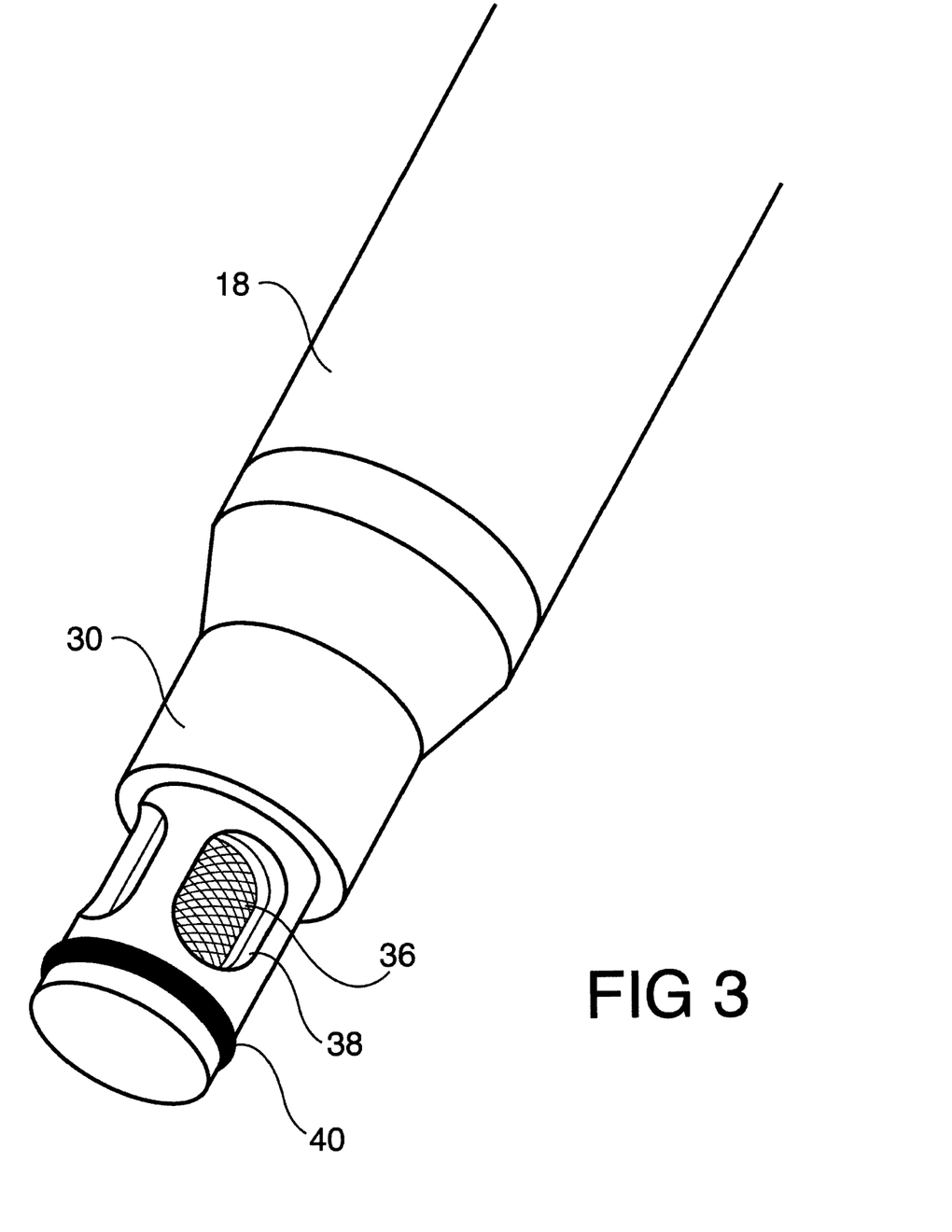
FIG. 3 is view of the testing end of the tester of FIG. 2 showing the details of the same.
Figure 4:
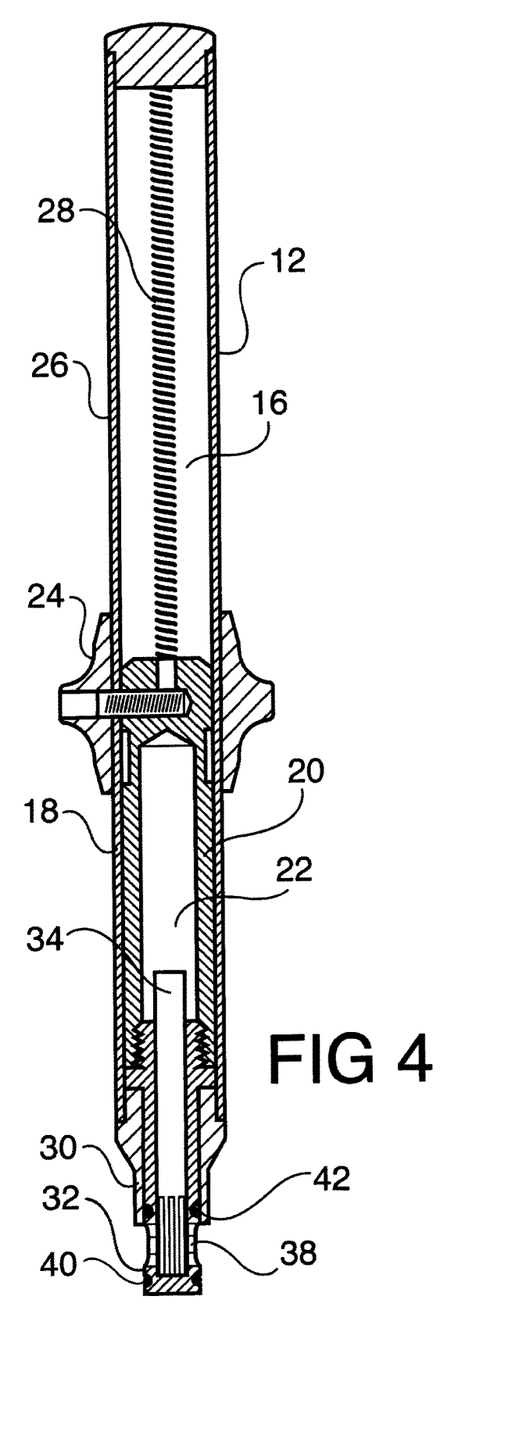
FIG. 4 is a cross-sectional view showing the interior of the tester shown in FIG. 2 in the open position.
Figure 5:
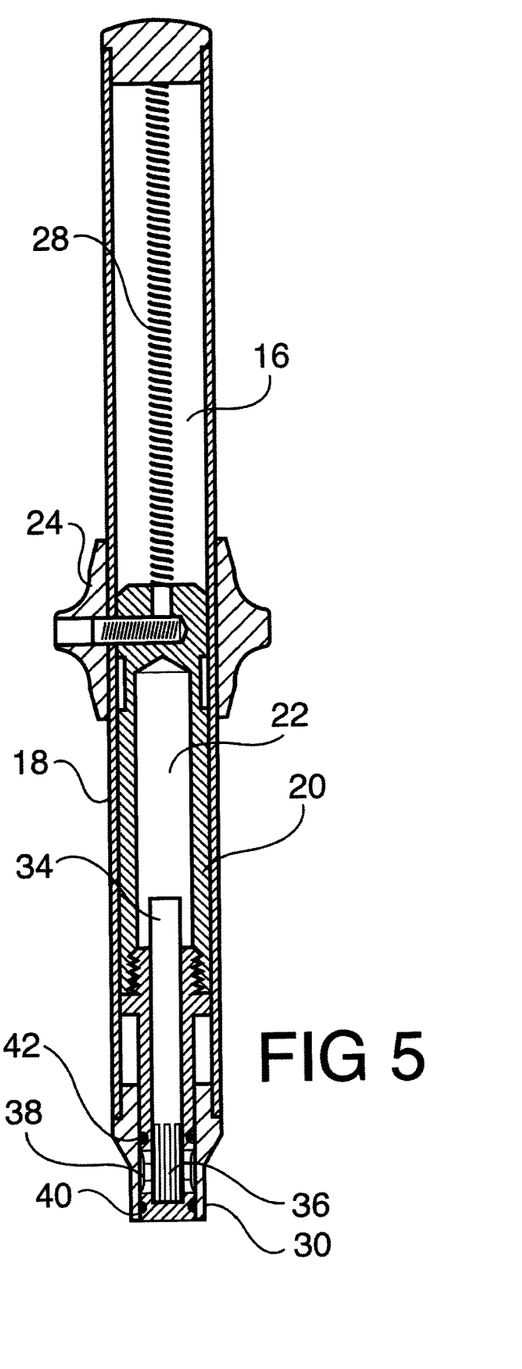
FIG. 5 is a cross-sectional view showing the interior of the tester shown in FIG. 1 in the closed position.

As shown in FIGS. 2 and 3, the nozzle 32 has a plurality of openings 38 around the circumference thereof. This permits the odorant from the nib 36 to be exposed when the nozzle extends outwardly from the housing as shown in FIG. 3. In this position, the nozzle can be placed under a patient's nose and, because the nib is within the interior of the nozzle 32, it cannot physically touch the patient's nose.

In order to prevent the odorant from being exposed when the nozzle is closed and in order to preserve the odorant and prevent it from being wasted, the nozzle 32 is provided with a pair of O-rings 40 and 42 that are located on either side of the openings 38. The O-rings 40 and 42 seal against the inner surface of the forward end of the housing 12.

Figure 6:
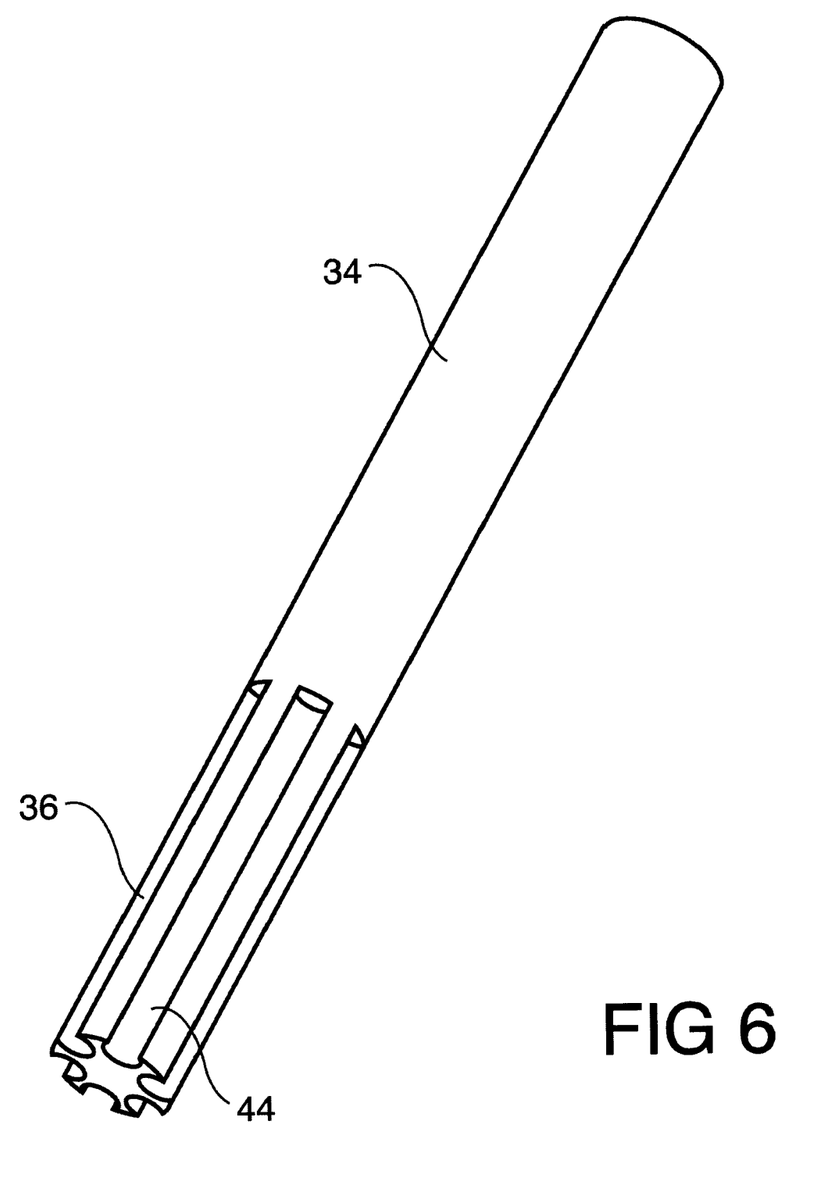
FIG. 6 is a perspective view of the wick and nib of the invention that carries the odorant.

To ensure that sufficient odorant vapors are released from the nib 36, the nib can be provided with a plurality of elongated grooves such as shown at 44 in FIG. 6. Alternatively, the nib could have ribs or holes passing therethrough. Substantially any configuration that would increase the exposed surface area of the nib could be utilized.

Figures 7A, 7B:
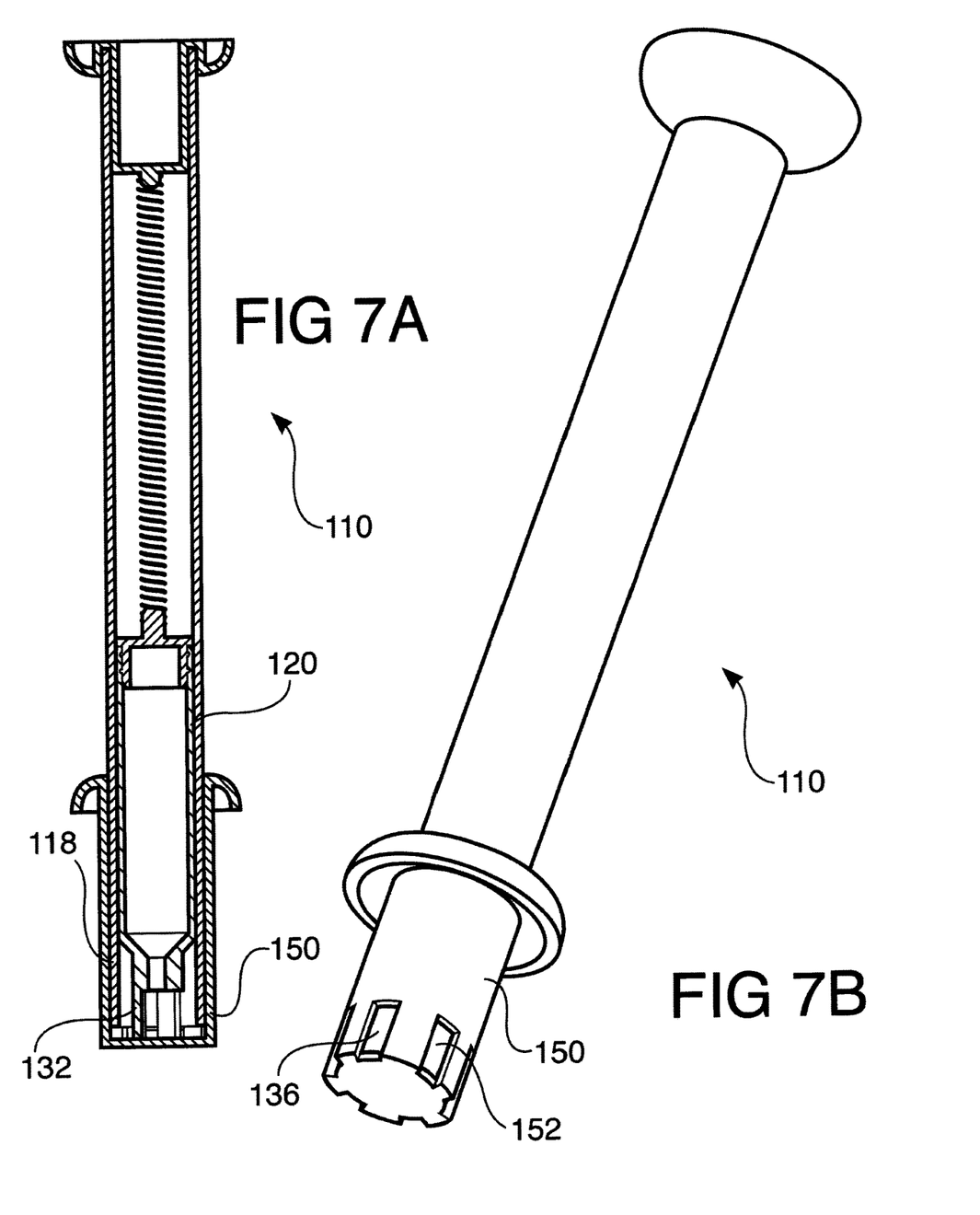
FIGS. 7A and 7B are cross-sectional and perspective views of an alternative embodiment of the olfactory tester of the invention.

The embodiment of the invention 110 shown in FIGS. 7A and 7B shares many of the features of the previously described embodiments. In FIGS. 7A and 7B, however, the nozzle 132 is normally covered by the forward end 118 of the housing and within the end cap 150. When the end cap 150 is moved forwardly, the odorant cylinder 120 along with the nozzle 132 moves forwardly beyond the end of the forward end 118. In this position, the nozzle 132 is no longer covered by the end 118 and the vapors from the nib 136 are free to pass through the plurality of openings 152 in the end cap 150 to the outside of the device.

Furthermore, in order to increase the amount of odorant vapor that is emitted, it may be beneficial to apply air pressure to the area around the reservoir. This can be accomplished by the use of a miniature fan located within the device. The fan could be activated manually or whenever the collar 24 or the end cap 150 is moved forward.

The present invention may be embodied in other specific forms without departing from the spirit or essential attributes thereof and accordingly, reference should be made to the appended claims rather than to the foregoing specification as indicating the scope of the invention.

The invention claimed is:

1. A hand held olfactory tester comprising:
an elongated housing having a forward portion and a rear portion, the forward portion including an opening adjacent the forward most end thereof;
a single odorant chamber located within said forward portion and containing an odorant therein, said single odorant chamber having a nozzle at the forward end thereof and being moveable axially between a forward position and a backward position within said housing;
a wick having a rear end located within said odorant chamber and a forward end extending forwardly thereof into said nozzle;
means for moving said odorant chamber along with said wick between said forward and backward positions, said moving means including a thumb engagable member located on the exterior of said housing intermediate the ends thereof and is engagable by a person holding said housing;
spring means for biasing said odorant chamber backwardly into its backward position;
said forward end of said wick being exposed to the outside of said housing through said nozzle and through said opening in said housing when said odorant chamber and said wick are moved into their forward position so that vapors from the odorant that had been wicked to the forward end of said wick can be smelled by a patient, and
means for sealing the forward end of said wick from the outside of said housing when said wick is in its backward position to prevent vapors from escaping from said housing, said sealing means including an O-ring located between the forward end of said nozzle and said forward most end of said housing.

2. The hand held olfactory tester as claimed in claim 1 wherein said nozzle includes an outer cylindrical wall and a plurality of openings in said cylindrical wall.

3. The hand held olfactory tester as claimed in claim 2 wherein said O-ring is carried by said nozzle.

4. The hand held olfactory tester as claimed in claim 3 including a second O-ring carried by said nozzle, one of said O-rings being located forward of said plurality of openings and the other of said O-rings being located rearwardly of said plurality of openings.

5. The hand held olfactory tester as claimed in claim 1 wherein said spring means includes an elongated spring located primarily in said rear portion of said housing.

6. The hand held olfactory tester as claimed in claim 1 wherein said thumb engagable member includes a collar surrounding said housing.

7. The hand held olfactory tester as claimed in claim 1 wherein said forward end of said wick includes means for increasing the surface area thereof to ensure that sufficient odor vapors are released.

8. The hand held olfactory tester as claimed in claim 7 wherein said means for increasing includes a plurality of grooves formed in said forward end of said wick.

\* \* \* \* \*